US009380981B2

(12) United States Patent
Kang et al.

(10) Patent No.: US 9,380,981 B2
(45) Date of Patent: Jul. 5, 2016

(54) PHOTOACOUSTIC MONITORING TECHNIQUE WITH NOISE REDUCTION

(71) Applicant: Covidien LP, Mansfield, MA (US)

(72) Inventors: DongYel Kang, Irvine, CA (US); Youzhi Li, Longmont, CO (US); Qiaojian Huang, Broomfield, CO (US); William Kit Dean, Castle Pines, CO (US)

(73) Assignee: Covidien LP, Mansfield, MA (US)

( * ) Notice: Subject to any disclaimer, the term of this patent is extended or adjusted under 35 U.S.C. 154(b) by 233 days.

(21) Appl. No.: 13/836,531

(22) Filed: Mar. 15, 2013

(65) Prior Publication Data

US 2014/0275941 A1    Sep. 18, 2014

(51) Int. Cl.
| | |
|---|---|
| *A61B 8/00* | (2006.01) |
| *A61B 5/00* | (2006.01) |
| *A61B 5/029* | (2006.01) |
| *A61B 5/08* | (2006.01) |
| *A61B 5/0275* | (2006.01) |
| *A61B 5/145* | (2006.01) |

(52) U.S. Cl.
CPC .............. *A61B 5/7278* (2013.01); *A61B 5/0095* (2013.01); *A61B 5/029* (2013.01); *A61B 5/0275* (2013.01); *A61B 5/08* (2013.01); *A61B 5/7203* (2013.01); *A61B 5/1451* (2013.01); *A61B 5/7228* (2013.01); *A61B 2562/0233* (2013.01)

(58) Field of Classification Search
CPC .. A61B 5/7278; A61B 5/0275; A61B 5/7203; A61B 5/08; A61B 5/029; A61B 5/0095; A61B 5/7228; A61B 2562/0233; A61B 5/1451

USPC ................... 600/437–469, 473–480
See application file for complete search history.

(56) References Cited

U.S. PATENT DOCUMENTS

| | | |
|---|---|---|
| 5,151,590 A | 9/1992 | Ryuichi et al. |
| 5,348,002 A | 9/1994 | Caro |
| 5,348,003 A | 9/1994 | Caro |
| 5,616,826 A | 4/1997 | Pellaux et al. |

(Continued)

FOREIGN PATENT DOCUMENTS

| | | |
|---|---|---|
| JP | 27259918 A2 | 10/2007 |
| WO | WO9851212 A1 | 11/1998 |
| WO | WO2007051066 | 5/2007 |

OTHER PUBLICATIONS

Newman, E.V., et al. "The Dye Dilution Method for Describing the Central Circulation: An Analysis of Factors Shaping the Time-Concentration Curves," Ciriculation. 1951; 4:735-746; DOI: 10.1161/01. CIR.4.5.735. Copyright 1951 American Heart Association, Inc. Print ISSN: 0009-7322. Online ISSN: 1524-4539.

(Continued)

*Primary Examiner* — Sanjay Cattungal
(74) *Attorney, Agent, or Firm* — Fletcher Yoder, P.C.

(57) ABSTRACT

Various methods and systems for photoacoustic patient monitoring are provided. A photoacoustic system includes a light emitting component that emits one or more wavelengths of light into an interrogation region of a patient and an acoustic detector that detects acoustic energy generated by the interrogation region of the patient in response to the emitted light. The system also includes an optical detector that detects the emitted light and provides a signal that is used as an input to remove noise from the signal generated by the acoustic detector.

19 Claims, 7 Drawing Sheets

(56) References Cited

U.S. PATENT DOCUMENTS

| | | | |
|---|---|---|---|
| 5,840,023 A | 11/1998 | Oraevsky et al. | |
| 5,941,821 A | 8/1999 | Chou | |
| 6,049,728 A | 4/2000 | Chou | |
| 6,299,583 B1 | 10/2001 | Eggers et al. | |
| 6,309,352 B1 | 10/2001 | Oraevsky et al. | |
| 6,403,944 B1 | 6/2002 | MacKenzie et al. | |
| 6,405,069 B1 | 6/2002 | Oraevsky et al. | |
| 6,466,806 B1 | 10/2002 | Geva et al. | |
| 6,498,942 B1 | 12/2002 | Esenaliev et al. | |
| 6,751,490 B2 | 6/2004 | Esenaliev et al. | |
| 6,833,540 B2 | 12/2004 | MacKenzie et al. | |
| 6,846,288 B2 | 1/2005 | Nagar et al. | |
| 6,939,307 B1 | 9/2005 | Dunlop | |
| 7,322,972 B2 | 1/2008 | Viator et al. | |
| 7,387,027 B2 | 6/2008 | Choi et al. | |
| 7,398,672 B2 | 7/2008 | Riddle | |
| 7,430,445 B2 | 9/2008 | Esenaliev et al. | |
| 7,447,388 B2 | 11/2008 | Bates et al. | |
| 7,483,731 B2 | 1/2009 | Hoarau et al. | |
| 7,500,953 B2 | 3/2009 | Oraevsky et al. | |
| 7,515,948 B1 | 4/2009 | Balberg et al. | |
| 7,680,522 B2 | 3/2010 | Andersohn et al. | |
| 8,121,663 B2 | 2/2012 | Peyman et al. | |
| 8,135,450 B2 | 3/2012 | Esenaliev et al. | |
| 8,144,327 B2 | 3/2012 | Nakajima et al. | |
| 8,234,907 B2 | 8/2012 | Helwegen et al. | |
| 8,289,517 B2 | 10/2012 | Miklos et al. | |
| 8,306,593 B2 | 11/2012 | Hwang et al. | |
| 8,322,190 B2 | 12/2012 | Kalkman et al. | |
| 8,352,005 B2 | 1/2013 | Esenaliev et al. | |
| 8,454,512 B2* | 6/2013 | Wang et al. | 600/437 |
| 9,055,869 B2* | 6/2015 | Li et al. | |
| 2002/0172323 A1 | 11/2002 | Karellas et al. | |
| 2003/0216663 A1 | 11/2003 | Jersey-Willuhn et al. | |
| 2005/0054907 A1 | 3/2005 | Page et al. | |
| 2005/0150309 A1 | 7/2005 | Beard | |
| 2005/0254058 A1 | 11/2005 | Alphonse | |
| 2006/0224053 A1 | 10/2006 | Black et al. | |
| 2006/0253007 A1 | 11/2006 | Cheng et al. | |
| 2006/0253043 A1 | 11/2006 | Zhang et al. | |
| 2007/0015992 A1 | 1/2007 | Filkins et al. | |
| 2007/0059247 A1 | 3/2007 | Lindner et al. | |
| 2007/0093702 A1 | 4/2007 | Yu et al. | |
| 2007/0197886 A1 | 8/2007 | Naganuma et al. | |
| 2007/0232872 A1 | 10/2007 | Prough et al. | |
| 2007/0239003 A1 | 10/2007 | Shertukde et al. | |
| 2008/0255433 A1 | 10/2008 | Prough et al. | |
| 2010/0016731 A1 | 1/2010 | Eggers et al. | |
| 2010/0030137 A1 | 2/2010 | Hall et al. | |
| 2010/0094144 A1 | 4/2010 | Doron | |
| 2010/0152591 A1 | 6/2010 | Yu et al. | |
| 2010/0268042 A1* | 10/2010 | Wang et al. | 600/322 |
| 2010/0298689 A1 | 11/2010 | Wang | |
| 2011/0028806 A1 | 2/2011 | Merritt et al. | |
| 2011/0071373 A1 | 3/2011 | Li et al. | |
| 2011/0071598 A1 | 3/2011 | McKenna | |
| 2011/0083509 A1 | 4/2011 | Li et al. | |
| 2011/0190612 A1 | 8/2011 | McKenna et al. | |
| 2012/0029829 A1 | 2/2012 | Li et al. | |
| 2012/0052018 A1 | 3/2012 | Bellott et al. | |
| 2012/0172686 A1 | 7/2012 | Esenaliev et al. | |
| 2012/0197117 A1 | 8/2012 | Picot et al. | |
| 2012/0220844 A1 | 8/2012 | Baker, Jr. | |
| 2013/0109941 A1 | 5/2013 | Li et al. | |
| 2013/0109947 A1 | 5/2013 | Wood | |
| 2013/0109948 A1 | 5/2013 | Li | |
| 2013/0123590 A1 | 5/2013 | Naganuma et al. | |
| 2013/0123591 A1 | 5/2013 | Naganuma et al. | |
| 2013/0137959 A1 | 5/2013 | Lisogurski et al. | |
| 2013/0137960 A1* | 5/2013 | Lisogurski et al. | 600/407 |
| 2013/0144147 A1* | 6/2013 | Li et al. | 600/407 |
| 2013/0144148 A1* | 6/2013 | Li et al. | 600/407 |
| 2013/0286379 A1* | 10/2013 | Li et al. | 356/40 |
| 2014/0049770 A1* | 2/2014 | Li et al. | 356/40 |
| 2014/0275943 A1 | 9/2014 | Kang et al. | |

OTHER PUBLICATIONS

Pan, Z., "Face Recognition in Hyperspectral Images," IEEE Transactions on Pattern Analysis and Machine Intelligence, vol. 25, No. 12, pp. 1552-1560, Dec. 2003.

Esenaliev, R.O., et al., "Continuous, noninvasive monitoring of total hemoglobin concentration by an optoacoustic technique," vol. 43, No. 17, pp. 3401-3407, Applied Optics, Jun. 10, 2004.

Xu et al., Photoacoustic imaging in biomedicine, Rev.Sci.Instrum. 77, 041101 (2006).

Reuter et al., "Cardiac Output Monitoring Using Indicator-Dilution Techniques: Basics, Limits, and Perspectives," Anesthesia Analog 2010, 110 799-811.

Sarchen, E., et al., Novel, Focused Optoacoustic Transducers for Accurate Monitoring of Total Hemoglobin Concentration and Oxyhemoglobin Saturation: Pre-clinical and Clinical Tests; Proc. of SPIE vol. 7564 756411-3; Downloaded from SPIE Digital Library on Apr. 6, 2010 to 72.37.250.177. Terms of Use: http://spiedl.org/terms.

Petrov, I.Y., et al., "Optoacoustic monitoring of cerebral venous blood oxygenation though intact scalp in large animals," Feb. 13, 2012/vol. 20, No. 4/Optics Express 4159-4167.

Nelligan et al., "Intro to Ultrasonic Phased Array", http://www.olympus-ims.com/en/ultrasonics/intro-to-pa/, Oct. 23, 2014, pp. 1-9.

U.S. Appl. No. 13/840,944, filed Mar. 15, 2013.

* cited by examiner

PHOTOACOUSTIC MONITORING TECHNIQUE WITH NOISE REDUCTION

BACKGROUND

The present disclosure relates generally to medical devices and, more particularly, to the use of photoacoustic spectroscopy in patient monitoring.

This section is intended to introduce the reader to various aspects of art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

In the field of medicine, medical practitioners often desire to monitor certain physiological characteristics of their patients. Accordingly, a wide variety of devices have been developed for monitoring patient characteristics. Such devices provide doctors and other healthcare personnel with the information they need to provide healthcare for their patients. As a result, such monitoring devices have become an indispensable part of modern medicine. For example, clinicians may wish to monitor a patient's blood flow to assess cardiac function. In particular, clinicians may wish to monitor a patient's cardiac output. The determination of cardiac output may provide information useful for the diagnosis and treatment of various disease states or patient abnormalities. For example, in cases of pulmonary hypertension, a clinical response may include a decrease in cardiac output.

Accordingly, there are a variety of clinical techniques that may be used for analyzing cardiac output. In one technique, an indicator, such as a dye or saline solution, is injected into a circulatory system of a patient, and information about certain hemodynamic parameters may be determined by assessing the dilution of the indicator after mixing with the bloodstream. However, such techniques involve invasive artery catheters for detecting the dilution of the indicator. Other techniques may involve radioactive indicators that are easier to detect, but expose the patient to radioactivity and involve expensive detection equipment.

BRIEF DESCRIPTION

Provided herein are non-invasive photoacoustic techniques that are capable of measuring indicator dilution. For example, for patients with an indicator solution injected into a vein, photoacoustic monitoring techniques may be used to measure dilution of the indicator in a downstream artery after mixing in the blood. The extent of dilution relates to cardiac output and other hemodynamic parameters. Such techniques may involve a photoacoustic sensor and/or an associated monitoring system or methods used in conjunction with such sensors and/or systems.

The disclosed embodiments include a photoacoustic monitoring system. The photoacoustic monitoring system includes a memory that stores instructions for: receiving a first signal from an acoustic detector configured to detect a photoacoustic effect from light emitted into a patient's tissue, wherein the first signal is representative of an indicator dilution; receiving a second signal from a photodetector configured to detect the light wherein the first signal and the second signal include an overlapping time period; and determining a physiological parameter based at least in part on the first signal and the second signal. The photoacoustic monitoring system also includes a processor configured to execute the instructions.

The disclosed embodiments also include a method performed using a processor. The method includes the steps of receiving a first signal from an acoustic detector configured to detect a photoacoustic effect from light emitted into a patient's tissue; receiving a second signal from a photodetector configured to detect the light; correcting the first signal based on the second signal to generate a corrected first signal; and determining a physiological parameter based on the corrected first signal.

The disclosed embodiments also include a photoacoustic sensor that includes a light emitting component configured to emit one or more wavelengths of light into a tissue of a patient; an acoustic detector configured to detect a photoacoustic effect from the light emitted into the patient's tissue; and an optical detector configured to detect the light scattering through the patient's tissue.

BRIEF DESCRIPTION OF THE DRAWINGS

Advantages of the disclosed techniques may become apparent upon reading the following detailed description and upon reference to the drawings in which.

DETAILED DESCRIPTION OF SPECIFIC EMBODIMENTS

One or more specific embodiments of the present techniques will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

In certain medical contexts it may be desirable to ascertain various localized physiological parameters, such as parameters related to individual blood vessels or other discrete components of the vascular system. Examples of such parameters may include oxygen saturation, hemoglobin concentration, perfusion, and so forth, for an individual blood vessel. In one approach, measurement of such localized parameters is achieved via photoacoustic (PA) spectroscopy. Photoacoustic spectroscopy uses light directed into a patient's tissue to generate acoustic waves that may be detected and resolved to determine localized physiological information of interest. In particular, the light energy directed into the tissue may be provided at particular wavelengths that correspond to the absorption profile of one or more blood or tissue constituents of interest. In certain embodiments, the light is emitted as pulses (i.e., pulsed photoacoustic spectroscopy), though in other embodiments the light may be emitted in a continuous manner (i.e., continuous photoacoustic spectroscopy). The light absorbed by the constituent of interest results in a proportionate increase in the kinetic energy of the constituent (i.e., the constituent is heated), which results in the generation of acoustic waves. The acoustic waves may be detected and used to determine the amount of light absorption, and thus the quantity of the constituent of interest, in the illuminated region. For example, the detected ultrasound energy may be proportional to the optical absorption coefficient of the blood or tissue constituent and the fluence of light at the wavelength of interest at the localized region being interrogated (e.g., a specific blood vessel).

When an indicator is injected into a vein in a cardiovascular system, a diluted temporal profile of the indicator may be measured in a downstream artery to estimate the hemodynamic properties. As provided herein, the dilution measurement may be performed with a photoacoustic monitoring technique that, in particular embodiments, does not use an invasive artery catheter to capture the dilution of the indicator in the artery. Algorithms applied to photoacoustic indicator dilution curves may be used to estimate hemodynamic properties, such as cardiac output. However, in cases where the indicator dilution curves contain noise, such noise may come from multiple sources including patient respiration and/or perfusion and is complex to remove with signal processing techniques due to overlapping frequency ranges. Further, light is modulated in the tissue due to cardiac cycles and respiration to change the amount of the photoacoustic effect over the course of the measurement.

The present techniques use a photoacoustic optical light source not only to generate acoustic waves, but also to generate a separately detected optical signal. The detected optical signal may be used as an input to separate signal from noise in the detected acoustic signal. In one embodiment, a photoacoustic sensor includes a light source and a light detector as well as an acoustic detector. In another embodiment, a photoacoustic monitor is configured to receive a signal from a light detector and an acoustic detector and determine a physiological parameter based on a correlation, such as a negative correlation, between the acoustic detector signal and the light detector signal.

Figure 1:
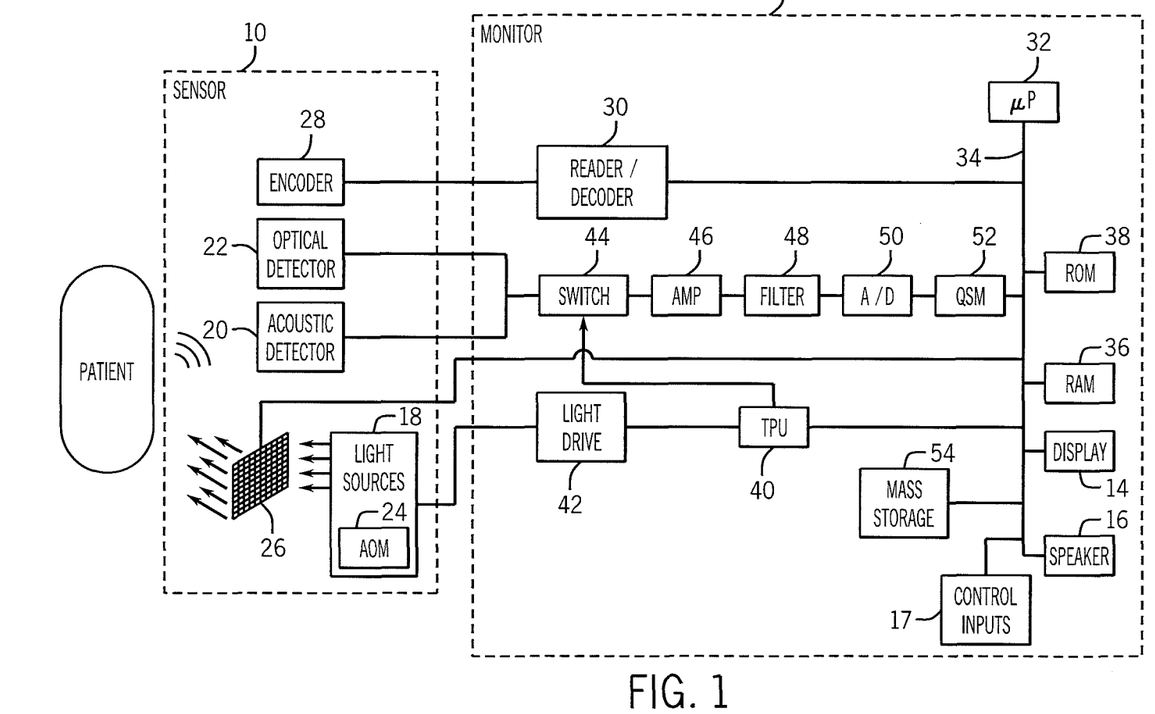
FIG. 1 is a block diagram of a patient monitor and photoacoustic sensor in accordance with an embodiment.

With the foregoing in mind, FIG. 1 depicts an example of a photoacoustic monitoring system 8 that may be utilized in determining cardiac output. The system 8 includes a photoacoustics sensor 10 and a monitor 12. Some photoacoustic systems 8 may include one or more photoacoustic sensors 10, as illustrated in FIG. 1, to generate physiological signals for different regions of a patient. For example, in certain embodiments, a single sensor 10 may have sufficient penetration depth to generate physiological signals from deep vessels (e.g., pulmonary artery and/or pulmonary vein). In other embodiments, more than one (e.g., two sensors) sensor 10 may be used to monitor physiological parameters (e.g., oxygen saturation) of more superficial vessels (e.g., the jugular vein and the femoral vein). Further, a system 8 as contemplated may be used in conjunction with other types of medical sensors, e.g., pulse oximetry or regional saturation sensors, to provide input to a multiparameter monitor.

The sensor 10 may emit spatially modulated light at certain wavelengths into a patient's tissue and may detect acoustic waves (e.g., ultrasound waves) generated in response to the emitted light. The monitor 12 may be capable of calculating physiological characteristics based on signals received from the sensor 10 that correspond to the detected acoustic waves. The monitor 12 may include a display 14 and/or a speaker 16 which may be used to convey information about the calculated physiological characteristics to a user. Further, the monitor 12 may be configured to receive user inputs via control input circuitry 17. The sensor 10 may be communicatively coupled to the monitor 12 via a cable or, in some embodiments, via a wireless communication link.

In one embodiment, the sensor 10 may include a light source 18 and an acoustic detector 20, such as an ultrasound transducer. The disclosed embodiments may generally describe the use of continuous wave (CW) light sources to facilitate explanation. However, it should be appreciated that the photoacoustic sensor 10 may also be adapted for use with other types of light sources, such as pulsed light sources, in other embodiments. In certain embodiments, the light source 18 may be associated with one or more optical fibers for conveying light from one or more light generating components to the tissue site. The sensor 10 also includes an optical detector 22 that may be a photodetector, such as a silicon photodiode package, selected to receive light in the range emitted from the light source 18. In the present context, the optical detector 22 may be referred to as a detector, a photodetector, a detector device, a detector assembly or a detector component. Further, the detector 22 and light source 18 may be referred to as optical components or devices.

For example, in one embodiment the light source 18 may be one, two, or more light emitting components (such as light emitting diodes) adapted to transmit light at one or more specified wavelengths. In certain embodiments, the light source 18 may include a laser diode or a vertical cavity surface emitting laser (VCSEL). The laser diode may be a tunable laser, such that a single diode may be tuned to various wavelengths corresponding to a number of different absorbers of interest in the tissue and blood. That is, the light may be any suitable wavelength or wavelengths (such as a wavelength between about 500 nm to about 1100 nm or between about 600 nm to about 900 nm) that is absorbed by a constituent of interest in the blood or tissue. For example, wavelengths between about 500 nm to about 600 nm, corresponding with green visible light, may be absorbed by deoxyhemoglobin and oxyhemoglobin. In other embodiments, red wavelengths (e.g., about 600 nm to about 700 nm) and infrared or near infrared wavelengths (e.g., about 800 nm to about 1100 nm) may be used. In one embodiment, the selected wavelengths of light may penetrate between 1 mm to 3 cm into the tissue of the patient. In certain embodiments, the selected wavelengths may penetrate through bone (e.g., the rib cage) of the patient.

One problem that may arise in photoacoustic spectroscopy may be attributed to the tendency of the emitted light to diffuse or scatter in the tissue of the patient. As a result, light emitted toward an internal structure or region, such as a blood vessel, may be diffused prior to reaching the region so that amount of light reaching the region is less than desired. Therefore, due to the diffusion of the light, less light may be available to be absorbed by the constituent of interest in the target region, thus reducing the acoustic waves generated at the target region of interest, such as a blood vessel. To increase the precision of the measurements, the emitted light may be focused on an internal region of interest by modulating the intensity and/or phase of the illuminating light.

Accordingly, an acousto-optic modulator (AOM) 24 may modulate the intensity of the emitted light, for example, by using LFM techniques. The emitted light may be intensity modulated by the AOM 24 or by changes in the driving current of the LED emitting the light. The intensity modulation may result in any suitable frequency, such as from 1 MHz to 10 MHz or more. Accordingly, in one embodiment, the light source 18 may emit LFM chirps at a frequency sweep range approximately from 1 MHz to 5 MHz. In another embodiment, the frequency sweep range may be of approximately 0.5 MHz to 10 MHz. The frequency of the emitted light may be increasing with time during the duration of the chirp. In certain embodiments, the chirp may last approximately 0.1 second or less and have an associated energy of a 10 mJ or less, such as between 1 µJ to 2 mJ, 1-5 mJ, 1-10 mJ. In such an embodiment, the limited duration of the light may prevent heating of the tissue while still emitting light of sufficient energy into the region of interest to generate the desired acoustic waves when absorbed by the constituent of interest.

Additionally, the light emitted by the light source 18 may be spatially modulated, such as via a modulator 26. For example, in one embodiment, the modulator 26 may be a spatial light modulator, such as a Holoeye® LC-R 2500 liquid crystal spatial light modulator. In one such embodiment, the spatial light modulator may have a resolution of 1024×768 pixels or any other suitable pixel resolution. During operation, the pixels of the modulator 26 may be divided into subgroups (such as square or rectangular subarrays or groupings of pixels) and the pixels within a subgroup may generally operate together. For example, the pixels of a modulator 26 may be generally divided into square arrays of 10×10, 20×20, 40×40, or 50×50 pixels. In one embodiment, each subgroup of pixels of the modulator 26 may be operated independently of the other subgroups. The pixels within a subgroup may be operated jointly (i.e., are on or off at the same time) though the subgroups themselves may be operated independently of one another. In this manner, each subgroup of pixels of the modulator 26 may be operated so as to introduce phase differences at different spatial locations within the emitted light. That is, the modulated light that has passed through one subgroup of pixels may be at one phase and that phase may be the same or different than the modulated light that has passed through other subgroups of pixels, i.e., some segments or portions of the modulated light wavefront may be ahead of or behind other portions of the wavefront. In one embodiment, the modulator 26 may be associated with additional optical components (e.g., lenses, reflectors, refraction gradients, polarizers, and so forth) through which the spatially modulated light passes before reaching the tissue of the patient 22.

In one example, the acoustic detector 20 may be one or more ultrasound transducers, such as a focused ultrasound transducer, suitable for detecting ultrasound waves emanating from the tissue in response to the emitted light and for generating a respective optical or electrical signal in response to the ultrasound waves. For example, the acoustic detector 20 may be suitable for measuring the frequency and/or amplitude of the acoustic waves, the shape of the acoustic waves, and/or the time delay associated with the acoustic waves with respect to the light emission that generated the respective waves. In one embodiment an acoustic detector 20 may be an ultrasound transducer employing piezoelectric or capacitive elements to generate an electrical signal in response to acoustic energy emanating from the tissue of the patient 22, i.e., the transducer converts the acoustic energy into an electrical signal.

The disclosed embodiments depict reflectance-type sensor arrangements in which the light source 18 and the acoustic detector 20/light detector 22 are on the same side of the sensor. It should be understood that transmission-type arrangements are also contemplated in which the light source 18 and the acoustic detector 20/light detector 22 are on opposing sides of a tissue when applied to a patient. For a transmission mode sensor, the optical signal and the photoacoustic signal may have a positive correlation, as opposed to a reflectance-type configuration, which may have a negative correlation between these signals. Accordingly, the de-noising of the photoacoustic signal in such a transmission-type embodiment may take into account a positive correlation rather than a negative correlation, as in a reflectance-type embodiment.

In one implementation, the acoustic detector 20 may be a low finesse Fabry-Perot interferometer mounted on an optical fiber. In such an embodiment, the incident acoustic waves emanating from the probed tissue modulate the thickness of a thin polymer film. This produces a corresponding intensity modulation of light reflected from the film. Accordingly, the acoustic waves are converted to optical information, which is transmitted through the optical fiber to an upstream optical detector, which may be any suitable detector. In some embodiments, a change in phase of the detected light may be detected via an appropriate interferometry device which generates an electrical signal that may be processed by the monitor 12. The use of a thin film as the acoustic detecting surface allows high sensitivity to be achieved, even for films of micrometer or tens of micrometers in thickness. In one embodiment, the thin film may be a 0.25 mm diameter disk of 50 micrometer thickness polyethylene terephalate with an at least partially optically reflective (e.g., 40% reflective) aluminum coating on one side and a mirror reflective coating on the other (e.g., 100% reflective) that form the mirrors of the interferometer. The optical fiber may be any suitable fiber, such as a 50 micrometer core silica multimode fiber of numerical aperture 0.1 and an outer diameter of 0.25 mm.

The photoacoustic sensor 10 may include a memory or other data encoding component, depicted in FIG. 1 as an encoder 28. For example, the encoder 28 may be a solid state memory, a resistor, or combination of resistors and/or memory components that may be read or decoded by the monitor 12, such as via reader/decoder 30, to provide the monitor 12 with information about the attached sensor 10. For example, the encoder 28 may encode information about the sensor 10 or its components (such as information about the light source 18 and/or the acoustic detector 20). Such encoded information may include information about the configuration or location of photoacoustic sensor 10, information about the type of lights source(s) 18 present on the sensor 10, information about the wavelengths, light wave frequencies, chirp durations, and/or light wave energies which the light source(s) 18 are capable of emitting and the properties and/or detection range of the optical detector 22, information about the nature of the acoustic detector 20, and so forth. In certain embodiments, the information also includes a reference linear frequency modulation (LFM) chirp that was used to generate the actual LFM emitted light. This information may allow the monitor 12 to select appropriate algorithms and/or calibration coefficients for calculating the patient's physiological characteristics, such as the amount or concentration of a constituent of interest in a localized region, such as a blood vessel.

In one implementation, signals from the acoustic detector 20 (and decoded data from the encoder 28, if present) and the optical detector 22 may be transmitted to the monitor 12. The monitor 12 may include data processing circuitry (such as one or more processors 32, application specific integrated circuits (ASICS), or so forth) coupled to an internal bus 34. Also connected to the bus 34 may be a RAM memory 36, a ROM memory 38, a speaker 16 and/or a display 14. In one embodiment, a time processing unit (TPU) 40 may provide timing control signals to light drive circuitry 42, which controls operation of the light source 18, such as to control when, for how long, and/or how frequently the light source 18 is activated, and if multiple light sources are used, the multiplexed timing for the different light sources.

The TPU 40 may also control or contribute to operation of the acoustic detector 20 and/or the optical detector 22 such that timing information for data acquired using the acoustic detector 20 and/or the optical detector 22 may be obtained. Such timing information may be used in interpreting the acoustic wave data and/or in generating physiological information of interest from such acoustic data. For example, the timing of the acoustic data acquired using the acoustic detector 20 may be associated with the light emission profile of the light source 18 during data acquisition. Likewise, in one embodiment, data acquisition by the acoustic detector 20 may be gated, such as via a switching circuit 44, to account for differing aspects of light emission. For example, operation of the switching circuit 44 may allow for separate or discrete acquisition of data that corresponds to different respective wavelengths of light emitted at different times. Similarly, the data acquired from the optical detector 22 may be gated via the switched circuit 44.

The received signal from the acoustic detector 20 and/or the optical detector 22 may be amplified (such as via amplifier 46), may be filtered (such as via filter 48), and/or may be digitized if initially analog (such as via an analog-to-digital converter 50). The digital data may be provided directly to the processor 32, may be stored in the RAM 36, and/or may be stored in a queued serial module (QSM) 52 prior to being downloaded to RAM 36 as QSM 52 fills up. In one embodiment, there may be separate, parallel paths for separate amplifiers, filters, and/or A/D converters provided for different respective light wavelengths or spectra used to generate the acoustic data. Further, while the disclosed block diagram shows the signal from the optical detector 22 and the acoustic detector 20 being supplied to the same path (e.g., a path that may include a switch 44, amplifier 46, filter 48, A/D converter 50, and/or a QSM 52), it should be understood that these signals may be received and processed on separate paths or separate channels.

The data processing circuitry, such as processor 32, may derive one or more physiological characteristics based on data generated by the photoacoustic sensor 10. For example, based at least in part upon data received from the acoustic detector 20, the processor 32 may calculate the amount or concentration of a constituent of interest in a localized region of tissue or blood using various algorithms. In one embodiment, the processor 32 may calculate one or more of cardiac output, total blood volume, extravascular lung water, intrathoracic blood volume, and/or macro and microvascular blood flow from signals obtained from a signal sensor 10. In one embodiment, the processor 32 may calculate one or more of cardiac output, blood volume, extravascular lung water, intrathoracic blood volume, systemic and pulmonary blood flow, and/or macro and microvascular blood flow from signals obtained from a signal sensor 10. In certain embodiments, these algorithms may use coefficients, which may be empirically determined, that relate the detected acoustic waves generated in response to emitted light waves at a particular wavelength or wavelengths to a given concentration or quantity of a constituent of interest within a localized region. Further, the disclosed techniques include a correlation of a detected optical signal to the detected acoustic signal to remove noise.

In one embodiment, processor 32 may access and execute coded instructions, such as for implementing the algorithms discussed herein, from one or more storage components of the monitor 12, such as the RAM 36, the ROM 38, and/or a mass storage 54. Additionally, the RAM 36, ROM 38, and/or the mass storage 54 may serve as data repositories for information such as templates for LFM reference chirps, coefficient curves, and so forth. For example, code encoding executable algorithms may be stored in the ROM 38 or mass storage device 54 (such as a magnetic or solid state hard drive or memory or an optical disk or memory) and accessed and operated according to processor 32 instructions using stored data. Such algorithms, when executed and provided with data from the sensor 10, may calculate one or more physiological characteristics as discussed herein (such as the type, concentration, and/or amount of an indicator). Once calculated, the physiological characteristics may be displayed on the display 14 for a caregiver to monitor or review. Additionally, the calculated physiological characteristics, such as the hemodynamic parameters, may be sent to a multi-parameter monitor for further processing and display. Alternatively, the processor 32 may use the algorithms to calculate the cardiac output, and the cardiac output may be displayed on the display 14 of the monitor 12.

Figure 2A:
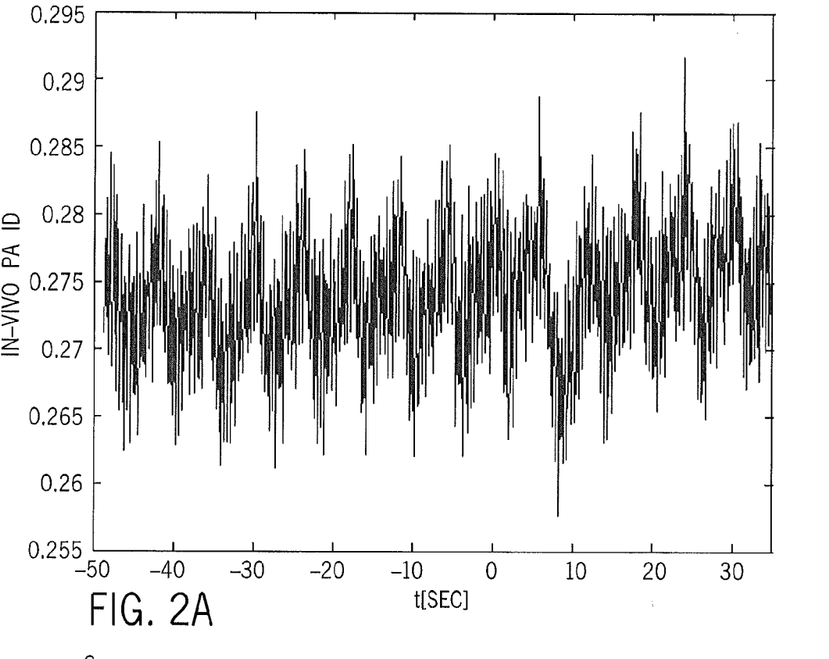
FIG. 2A is a plot of indicator dilution curves based on a photoacoustic detector signal.
Figure 2B:
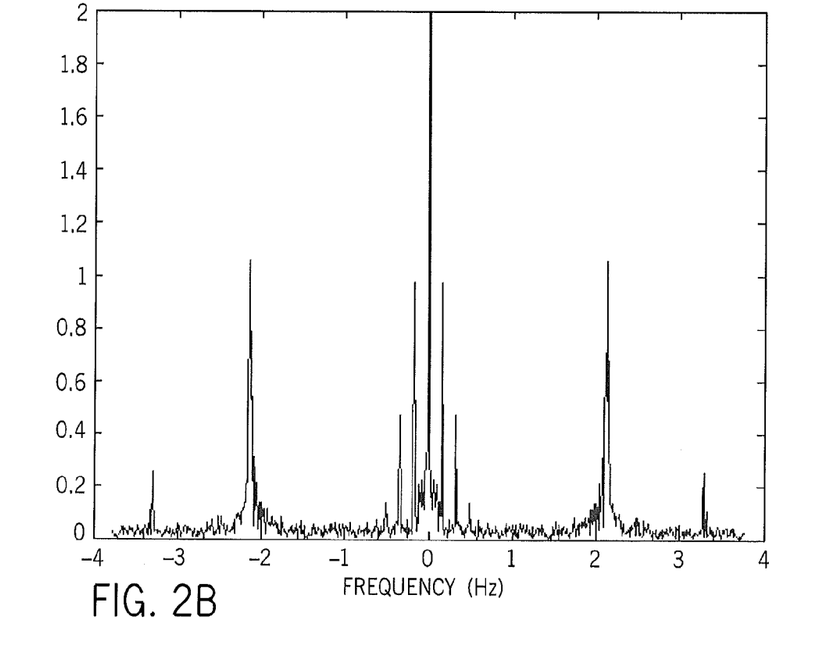
FIG. 2B is a plot of the frequency components of the photoacoustic detector signal of FIG. 2A.

The disclosed embodiments address the problem of noise in the received acoustic signal during photoacoustic monitoring of indicator dilution. FIG. 2A is an example of an in vivo photoacoustic indicator dilution curve for an isotonic injection that shows an example of such a noisy received signal over time. The zero time point represents the starting point of injection of the indicator. When the indicator dilution data as shown is further processed by algorithms to determine physiological parameters, the noise deteriorates the capability of such algorithms. The noise contribution of the signal may also be difficult to remove by filtering techniques because the frequency components of the noise and signal have a great deal of overlap. For example, filtering out the frequency components around 3.3 Hz in FIG. 2B does not show noticeable reduction of the respiratory-like noise in the indicator dilution curve because the physiological noise includes multiple frequency components. FIG. 2B shows the amplitude of the frequency components as determined by a Fourier transform of the photoacoustic indicator dilution curve of FIG. 2A.

Figure 3:
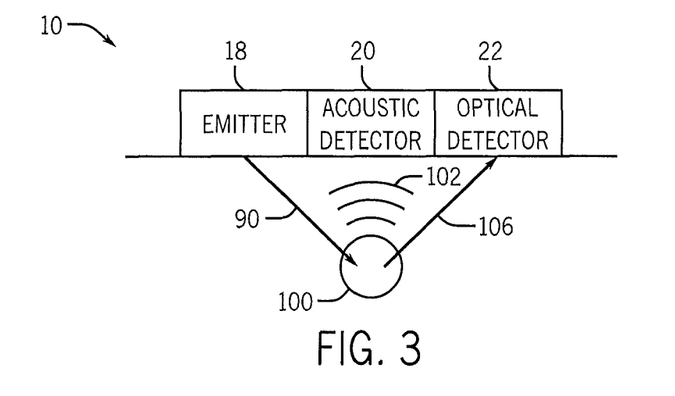
FIG. 3 illustrates a photoacoustic sensor assembly including an optical detector in accordance with an embodiment.

The signal of an optical detector (e.g., optical detector 22) correlates in a specific manner to the signal from the acoustic detector 20. Based on this correlation, the contribution of noise to the acoustic signal and the indicator dilution curves may be removed. In one embodiment, because the optical detector 22 is positioned relatively close to the acoustic detector and detects the optical signals scattered back from the tissue, the optical signals and the photoacoustic signals are negatively correlated to one another. Further, in one embodiment, the negative correlation may be associated with a reflectance-type sensor arrangement. As shown in FIG. 3, when the sensor 10 is applied to a patient, the light source 18 directs light 90 towards a target blood vessel 100. A portion of the light 90 is absorbed in the blood vessel 100 to generate acoustic waves 102. Another portion 106 scatters towards the optical detector 22 and is detected. Both the acoustic detector 20 and the optical detector 22 generate signals representative of the detected acoustic waves 100 and light 106, respectively. When a greater portion of the emitted light 90 is shunted away from and/or is absorbed by the optical detector 22, less light is available for generation of acoustic waves 100. Accordingly, the signals received at the acoustic detector 20 and the optical detector 22 may be negatively correlated. That is, when more light is received at the optical detector 22, smaller acoustic waves may be detected at the acoustic detector 20.

While the illustrated embodiment shows a sensor arrangement in which the acoustic detector 20 is between the light source 18 and the optical detector 22, it should be understood that other arrangements are contemplated. For example, the optical detector 22 may be positioned adjacent to the acoustic detector 20 but not along an axis connecting the light source 18 and the acoustic detector 20. In certain embodiments, the optical detector 22 and the acoustic detector 20 are directly next to or adjacent to one another. In one example of such an arrangement, the housings or support structures for these elements may contact one another. In this manner, the negative correlation between their signals may be enhanced. In another embodiment, the optical detector 22 and the acoustic detector 20 are spaced apart from one another. The geometry of the arrangement of the optical and acoustic components on the sensor 10 may influence the calibration of the sensor and may be provided as an input to certain algorithms. Accordingly, in one embodiment, sensor geometry information as well as other sensor identification information and/or calibration information may be stored in the encoder 28.

Figure 4:
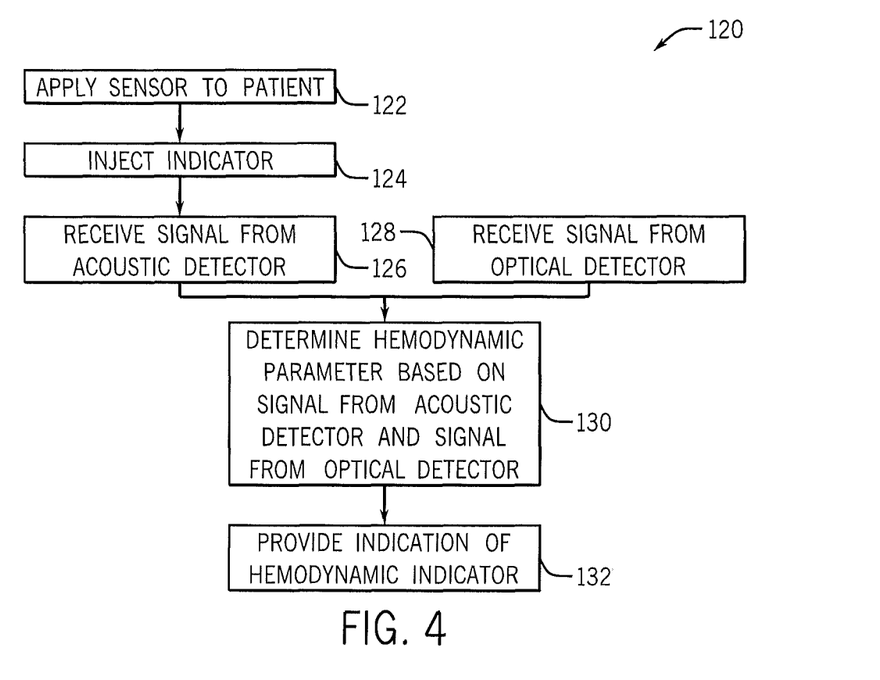
FIG. 4 is a flow diagram of a method of determining a hemodynamic parameter in accordance with an embodiment.

FIG. 4 is a process flow diagram illustrating a method for determining a hemodynamic parameter in conjunction with the photoacoustic sensors 10 and systems 8 as provided. The method is generally indicated by reference number 120 and includes various steps or actions represented by blocks. It should be noted that the method 120 may be performed as an automated procedure by a system, such as system 10. Further, certain steps or portions of the method may be performed by separate devices. For example, a first portion of the method 120 may be performed by a caregiver, while a second portion of the method 120 may be performed by a sensor and/or monitor 12 operating under processor control and in response to signals received from the sensor 10. In addition, insofar as steps of the methods disclosed herein are applied to the received signals, it should be understood that the received signals may be raw signals or processed signals. That is, the methods may be applied to an output of the received signals.

In certain embodiments, the method 120 begins with application of the photoacoustic sensor 10 to the patient at step 122. At step 124, an appropriate indicator is injected or otherwise supplied to the patient. In one embodiment, the caregiver may provide an input to the monitor 12 to indicate the indicator injection time point. In certain embodiments, the indicator may be provided as two or more indicators, which may be applied at the same time or different times, according to the desired measured parameter. In one embodiment, the indicator is an isotonic indictor. At step 126, a monitoring device, such as the monitor 12, receives an acoustic detector signal from the photoacoustic sensor 10 that is representative of detected photoacoustic waves in the tissue. At step 128, the monitor receives a corresponding optical detector signal (i.e., from the same or an overlapping time period as the acoustic detector signal) representative of detected light from the light source 18. Based in part on a determined correlation (e.g., negative correlation) or scaling factor between these signals, the desired hemodynamic parameter may be determined at step 130 and an indicator of the hemodynamic parameter may be provided by the monitor 12 at step 132.

Figure 5A:
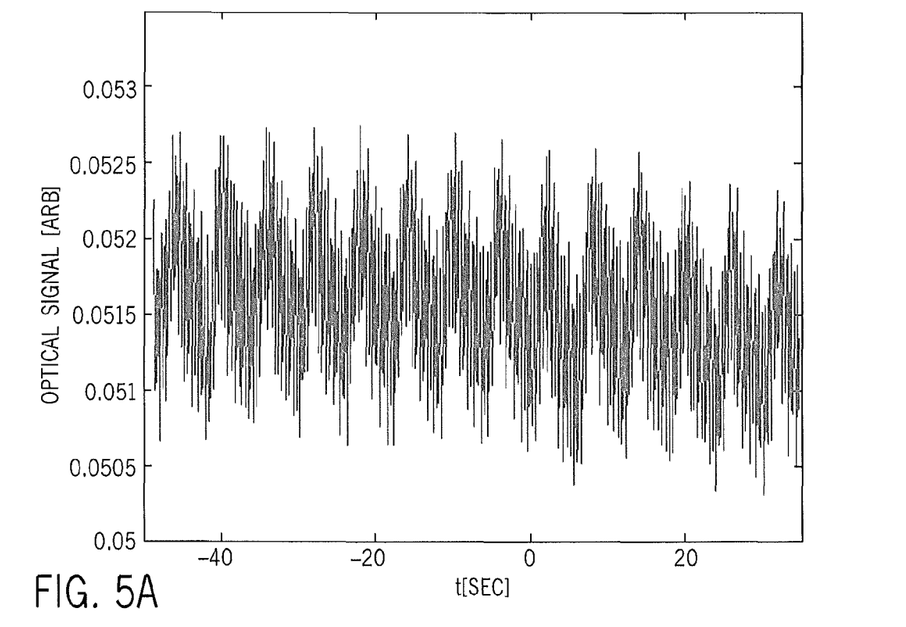
FIG. 5A is a plot of a corresponding optical detector signal to the acoustic detector signal of FIG. 2A.
Figure 5B:
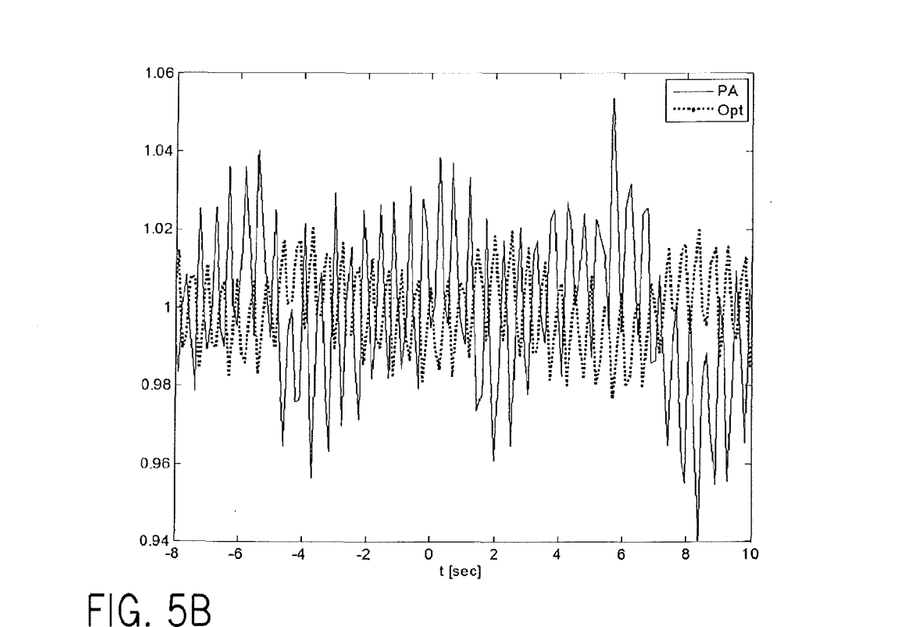
FIG. 5B is a plot the optical detector signal of FIG. 5A and the acoustic detector signal of FIG. 2A showing the negative correlation between these signals.

In one embodiment, the acoustic detector signal and the optical detector signal may have a negative correlation that can be used to remove noise from the photoacoustic signal. For example, a sensor 10 provided in a reflectance-type configuration may have a negative correlation. Because noise affects these signals in an inverse manner, the noise from the optical signal may be scaled and subtracted from the acoustic detector signal. FIG. 5A shows the measured optical signal that is associated with the photoacoustic indicator dilution curve shown in FIG. 2A. FIG. 5B is a mean-normalized photoacoustic curve and optical signal showing the negative correlation. In one embodiment, a scaling process may be applied to the signal from the acoustic detector 20 and the optical detector 22. Before the indicator injection, the baseline PA can be described as $$PA_b(t) = \Gamma t \mu_a(t) e^{-L\mu_{eff}(t)} \quad (1)$$

where, $\Gamma$ is the Gruneisen coefficient that is constant and $\mu_a$ and $\mu_{eff}$ are the absorption and background tissue optical properties, respectively. Both of them vary with physiological noise. Because the optical detector 22 is close to the acoustic detector 20 sensor (e.g., as part of sensor 10), the photoacoustic and optical signals are negatively correlated each other. For example, $\mu_a$ ($\mu_{eff}$) decreases (increases) the optical signal, which increases (decreases) the photoacoustic signal and vice versa. In $$Opt(t) \approx C_1 \left[ C_2 - \mu_a(t) e^{-L\mu_{eff}(t)} \right] \quad (2)$$

$C_1$ and $C_2$ are constants depending on the photoacoustic system and target tissue geometry. Conducting appropriate signal processing, Opt(t) can be scaled to $$Opt(t) = C\mu_a(t) e^{-L\mu_{eff}(t)} \quad (3)$$

where C is the constant given from the scaling process. Finally, the denoised photoacoustic signal becomes $$PA_b(t) = \left(\frac{1}{C}\right)\Gamma \quad (4)$$

where (1/C) contains constant (denoised) $\mu_a e^{-L\mu_{eff}}$.

Figure 6A:
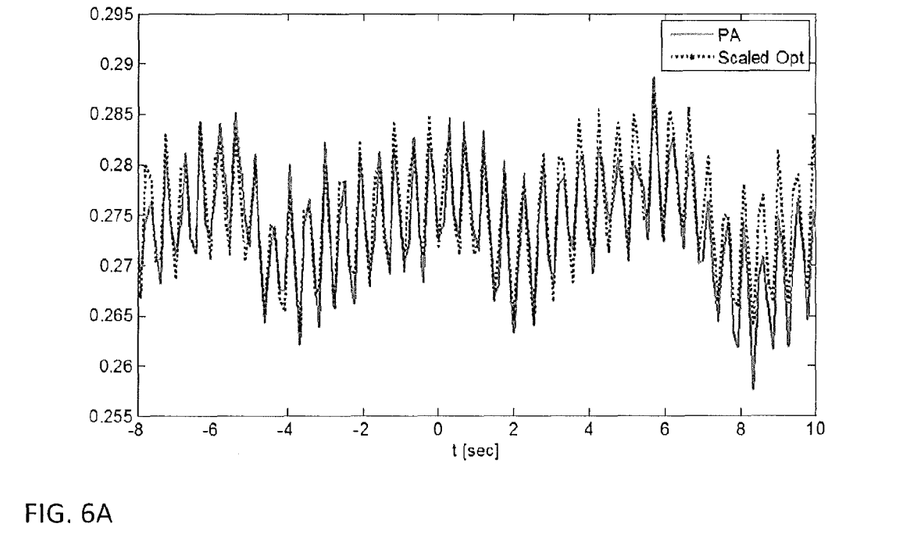
FIG. 6A is a plot of a scaled optical detector signal and the acoustic detector signal of FIG. 2A showing positive correlation.
Figure 6B:
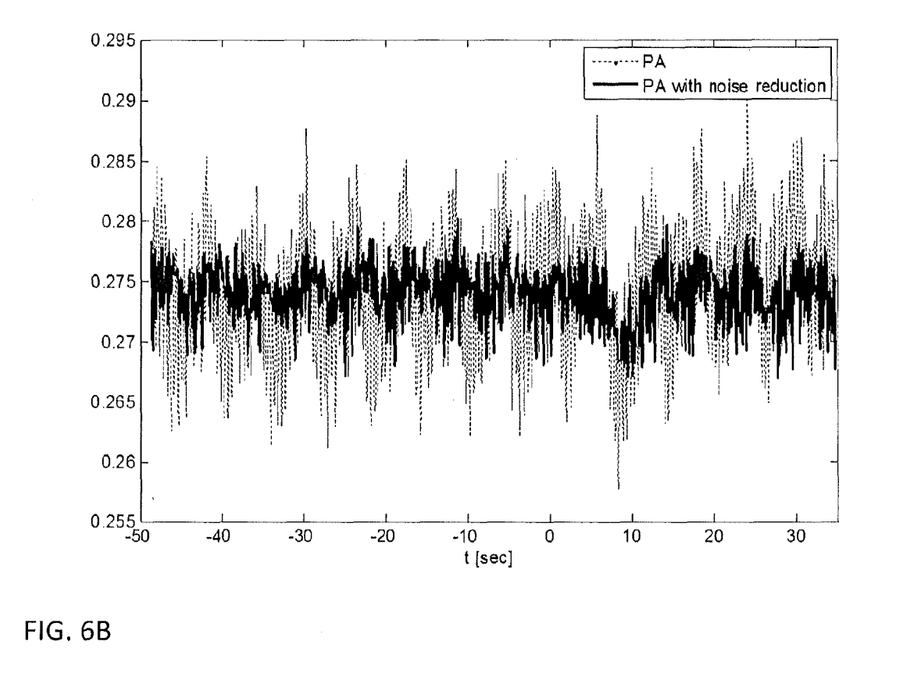
FIG. 6B is a plot the denoised acoustic detector signal and the uncorrected acoustic detector signal.
Figure 6C:
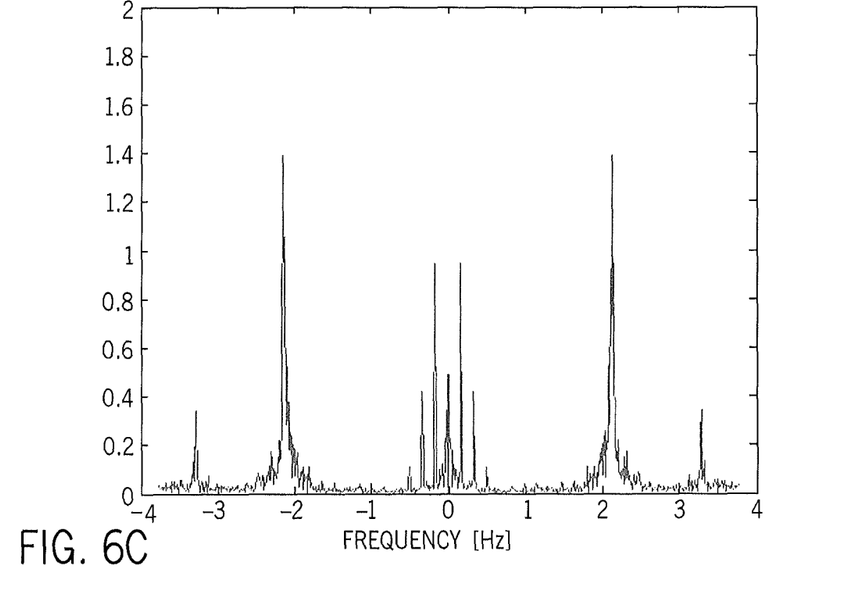
FIG. 6C is a plot of the frequency components of the scaled optical signal of FIG. 6A.
Figure 6D:
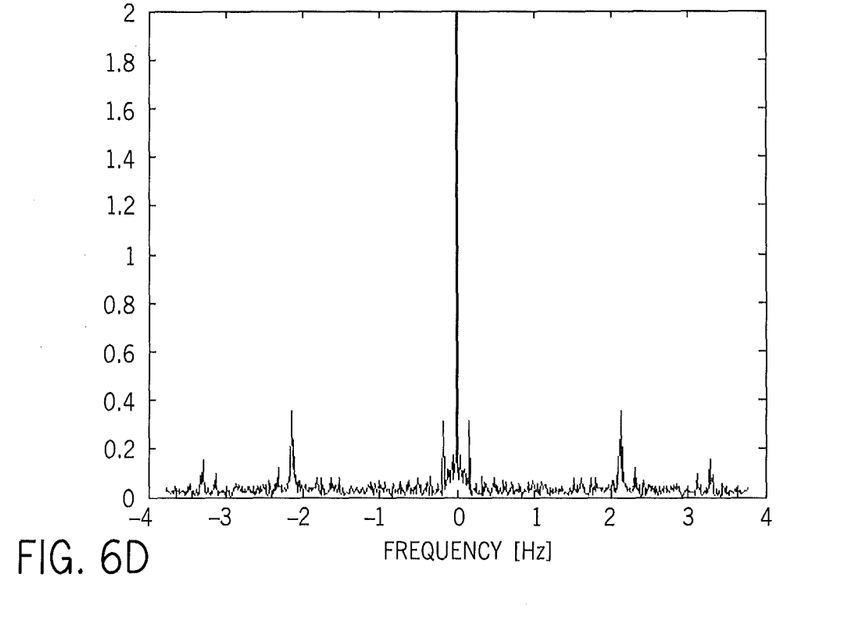
FIG. 6D is a plot of the frequency components of denoised acoustic signal of FIG. 6B.

FIG. 6A shows the scaled optical signal and the acoustic detector signal, and FIG. 6B shows the denoised acoustic signal after subtraction of the scaled optical signal. The acoustic detector signal without denoising was not resolvable when applied to cardiac output calculation algorithms. In contrast, the denoised acoustic signal provided estimates of cardiac output. FIG. 6C is the scaled optical signal in the frequency domain with the DC component removed, and FIG. 6D is the denoised acoustic signal in the frequency domain. A comparison of FIG. 2B and FIG. 6D shows an improved frequency profile for the signal components.

Figure 7:
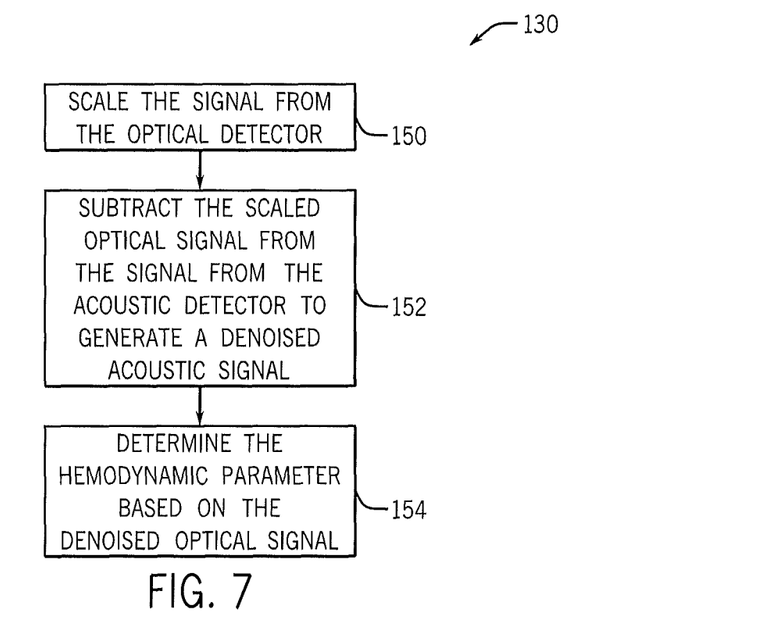
FIG. 7 is a flow diagram of a method of determining a hemodynamic parameter in accordance with an embodiment.

FIG. 7 is a flow diagram of one technique for performing step 130 of the method 120 shown in FIG. 4 that includes scaling algorithms, such as those disclosed herein. At step 150, the signal from the optical detector is scaled. The scaling process converts the negatively correlated optical detector signal to a positively correlated scaled optical detector signal. This scaled signal may be subtracted from the acoustic detector signal to yield a corrected or denoised signal at step 152. In one embodiment, the subtraction is performed in the frequency domain. In turn, the denoised signal may be used in conjunction with various algorithms for determining hemodynamic parameters at step 154. Further, the disclosed scaling techniques are one example of a correlation process for the optical detector signal and the acoustic detector signal. In other embodiments, these signals may be correlated using other suitable techniques, including linear and nonlinear processing techniques, comparisons and lookup tables for one or more extracted features or patterns of the optical detector signal and the acoustic detector signal, and/or polynomial analysis.

Figure 8:
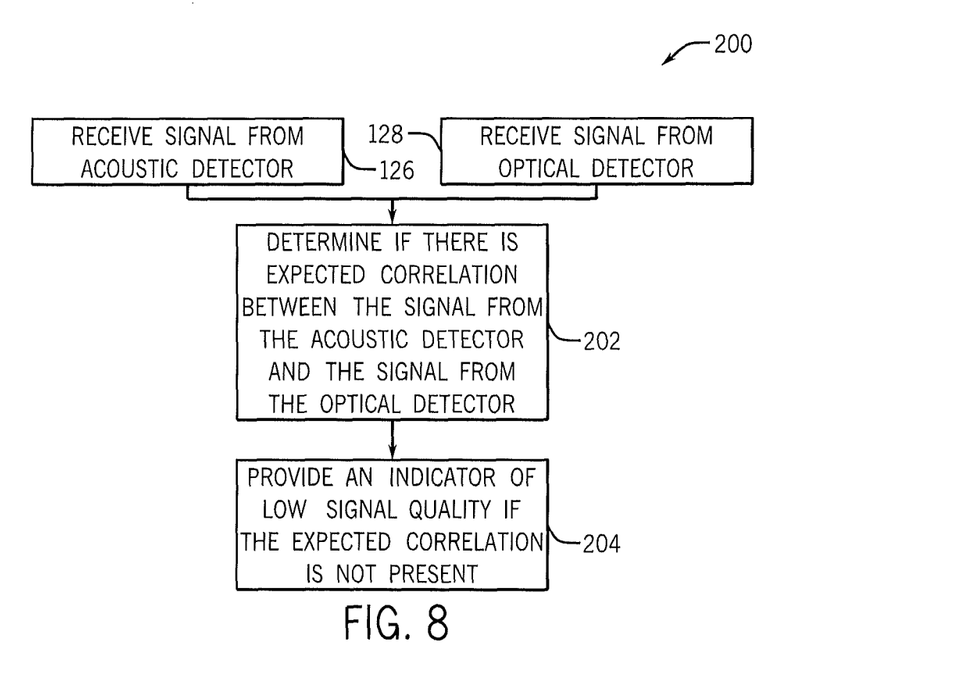
FIG. 8 is a flow diagram of a method of determining signal quality in accordance with an embodiment.

Further, in particular embodiment, the techniques provided herein may arbitrate between the uncorrected acoustic detector signal and the denoised signal. In other embodiments, the absence of an expected negative correlation between the optical detector signal and the acoustic detector signal may be used as an indicator of signal quality. FIG. 8 is a flow diagram of a method 200 that includes the steps 126 and 128 of receiving the acoustic detector signal and the optical detector signal, respectively. At step 202, the method 200 determines of the expected negative correlation between these signals is present. If the negative correlation is not present or is below a threshold, the method 200 provides an indication at step 204 of low signal quality. Such an indication may be a "CHECK SENSOR" message provided to the caregiver. If sufficient negative correlation is present (e.g., above a threshold), an indication of acceptable or good signal quality may be provided. In other embodiments, the correlation may be performed on the scaled signal rather than the unscaled optical detector signal. In such embodiments, the expected correlation for good signal quality may be positive rather than negative.

The system 8 (see FIG. 1) may also be configured to stop photoacoustic monitoring and/or change monitoring parameters based on the signal quality indication. Further, the method 200 may be used in conjunction with other disclosed methods (e.g., method 120), or may be used as a separate quality metric. For example, the method 200 may be used to arbitrate between different photoacoustic sensors 10 applied to the patient. For sensors 10 for which the signal is indicated as low quality, the system 8 may be configured to remove those signals as input to parameter determination. In other embodiments, the method 200 may be used to activate or deactivate supplemental optical detectors 22 associated with the sensor 10 and that may provide more favorable signal quality. For embodiments in which the photoacoustic sensor 10 is configured to measure additional parameters (e.g., optical parameters), the presence or absence of correlation may also be used to assess signal quality of the optical signal.

As discussed herein, the disclosed noise reduction techniques may be used to calculate physiological parameters, such as hemodynamic parameters. Accordingly, the disclosed embodiments may use the corrected and/or denoised acoustic detector signal as an input to hemodynamic parameter algorithms where the photoacoustic detector signal or the photoacoustic signal PA is denoted as an input. For example, the denoised photoacoustic detector signal may be used to determine cardiac output. In one embodiment, if $V_{It}$, the amount of an isotonic solution, is instantaneously injected at t=0 (i.e. the time of starting the injection is set to zero), the blood flow rate at the outlet point for the PA measurement is:

$$F = \frac{V_{It}}{\int_0^\infty \frac{V_I(t)}{V} dt} \quad (5)$$

where V and VI(t) are blood volume and isotonic volume rates during the unit time interval, $\Delta t$, respectively, in the sectional surface at the outlet point. Equation (5) indicates that the whole isotonic saline indicator passes through the outlet sectional surface after the injection. A photoacoustic signal is proportional to an absorption coefficient, $\mu_a$ of artery blood that is also proportional to a total hemoglobin concentration, $C_{tHb}$ in the blood vessel. Therefore, the background photoacoustic signal before the indicator injection can be $$PA_b = K \frac{tHb_b}{V} \quad (6)$$

where $tHb_b$ is the total hemoglobin in the unit blood volume V associated with $\Delta t$. K is the conversion coefficient from $C_{tHb}$ to a photoacoustic signal, which is assumed as constant during the indicator dilution measurement. K contains also other photoacoustic systematic effects, such as fluence in photoacoustic imaging. At the outlet point after the injection, the total hemoglobin in $tHb_b$ is decreased due to the added portion of the isotonic solution, $V_I(t)$. For this situation, the measured PA signal variation per $\Delta t$ can be described as $$PA(t) = K \cdot c_{tHb}(t) = K \frac{tHb_m(t)}{V_m(t) + V_I(t)} \quad (7)$$

where $V_m(t)+V_I(t)=V$. Since $V_I(t)$ is added to the total volume, V, the total hemoglobin in V, $tHb_m(t)$ is smaller than $tHb_b$. However, the hemoglobin concentration in pure blood (i.e. the blood without the isotonic solution) is not changed by the injection, so $$\frac{tHb_b}{V} = \frac{tHb_m(t)}{V_m(t)} \quad (8)$$

By substituting Eq. (8) to Eq. (7), the measured photoacoustic signal, PA(t) is $$PA(t) = K \frac{V_m(t) \cdot tHb_b}{V^2} = K \frac{[V - V_I(t)] \cdot tHb_b}{V^2} \quad (9)$$

Considering Eq. (6), Eq. (9) is further developed to $$PA(t) = PA_b \left[1 - \frac{V_I(t)}{V}\right]. \quad (10)$$

Here, it is assumed that $PA_b$ is stationary in time. Integrating both sides of Eq. (10) in time derives the blood flow rate as $$F = \frac{V_{lt}}{\left[\int_0^\infty dt - \int_0^\infty \frac{PA(t)}{PA_b}\right]} \quad (11)$$

where Eq. (5) is applied to the derivation of Eq. (11). Since a photoacoustic signal measured at the outlet point is decreased due to the isotonic injectate, the denominator of Eq. (11) indicates the area between the photoacoustic dilution curve and the normalized baseline, 1. The normalization in the integration of Eq. (11) is obtained during the derivation process, which is from that the photoacoustic signal is proportional to the inverse of the amount of an isotonic solution. Assumptions in other techniques may include (1) The system is "stationary" (flow F and the system configuration do not change with time), (2) indicator and fluid particles behave exactly the same, (3) indicator and fluid particles have identical transit time distributions, (4) each particle entering the system will leave it after a finite time, (5) there is no recirculation, and (6) dead volumes, meaning volumes that can be entered neither by flowing fluid particles nor by indicator particles. For the photoacoustic indicator dilution technique, several of these assumptions are removed (e.g., (2), (3), (4), (6) and (7)), leaving assumptions (1) and (5). Accordingly, the disclosed techniques also may improve the potential error sources by removing a number of assumptions. For thermodilution techniques, the temperature variation of injectates before the injection and unexpected loss of indicator temperature after injection are additional error sources that are also not associated with the disclosed techniques.

In another embodiment, the disclosed techniques may be used for estimating the extravascular lung water (EVLW) from double indicator dilution curves. For this double indicator technique, two indicators of isotonic and hypertonic bolus are injected into the venous circulation in series. The injected isotonic indicator passes through a vascular system without the interaction with lung tissues. The photoacoustic signal monitoring the variation of the isotonic solution concentration estimates a cardiac output. In contrast to the isotonic injection, the hypertonic indicator interacts with the lung due to the osmotic pressure difference between the vascular blood vessel and lung. The blood osmolarity is quickly increased from the injected hypertonic solution, which generates the osmolarity imbalance between the blood vessel and lung. By the osmolarity equilibrium time $t_e$, the lung water is transferred to the blood vessel due to the osmolarity imbalance. Right after the equilibrium time $t_e$, the osmolarity is reversed, so the lung starts absorbing the water from the blood by the second osmolarity equilibrium. Movement of solutes, such as NaCl, is small enough to ignore relative to water exchange. Since a photoacoustic signal is affected by the amount of absorption of incident photons due to the hemoglobin concentration in blood, isotonic, hypertonic, and lung water contents in the blood vessel decrease the measured photoacoustic signal. In the disclosed example, these two base signals are set to be different for a general application. The most significant problem of these different baselines is that it is not straightforward to find the equilibrium time because the photoacoustic signal decreasing is started from different background.

The osmolarity (n) of the vascular blood vessels with the hypertonic injectate can be described as $$\prod(t) = \left(\prod_h - \prod_b\right)\frac{\Delta V_h}{\Delta V} \quad (12)$$

where $\Pi_b$ and $\Pi_h$ are osmolarity of the pure blood and hypertonic solution, respectively, and are known. The amount of the lung water smeared into the blood vessel is omitted in Eq. (12) because the water transmittance is almost zero at the equilibrium time. Therefore, the osmolarity of the blood can be estimated at $t=t_e$, from Eq. (13), which is the same as that in the lung at that time. At constant temperature, the volume of the EVLW, $V_{LW}$, can be estimated by $$V_{LW} = \left|\frac{\Delta V_{LW}}{\Delta \prod_L}\right|\prod_L \quad (13)$$

where $\Delta V_{LW} = \Delta V_{LW}(t_e) - \Delta V_{LW}(t \le t_i)$
and $\Delta \Pi_L = \Pi_L(t_e) - \Pi_L(t \le t_i)$ are the amount of differences of the lung volume and osmolarity, respectively. $\Pi_L = \Pi_L(t \le t_i)$, which is also known. Note that the EVLW can be estimated once $\Delta V_{LW}$ and $$\frac{\Delta V_h}{\Delta V}$$

in Eq. (12) are found. The baseline photoacoustic signal is $$PA_b = Kc_{tHb} + PA_0 = K\frac{tHb_b}{\Delta V} + PA_0 \quad (14)$$

where $C_{tHb}$ is a hemoglobin concentration in a unit volume $\Delta V$ before the injection. K is the conversion coefficient from $C_{tHb}$ to a photoacoustic signal, which is assumed as constant during the indicator dilution measurement. The term $PA_0$ represents the photoacoustic signal from all photoacoustic sources insensitive to the indicator concentration change. It is assumed that $PA_0$ is the same for both dilution curves that is reasonable. After the hypertonic indicator injection, the photoacoustic signal becomes $$PA^h(t) = Kc_{tHb}(t) + PA_0 \quad (15)$$
where
$$c_{tHb}(t) = tHb_b / [\Delta V_b(t) + \Delta V_h(t) + \Delta V_{LW}(t)] \quad (16)$$

In Eq. (6), $\Delta V_b(t)$, $\Delta V_h(t)$, and $\Delta V_{LW}(t)$ indicate volumes of the blood, hypertonic, and lung water injected into the blood during dt, respectively. Since $$\frac{tHb_b}{\Delta V} = \frac{tHb_b(t)}{\Delta V(t)}$$

Eq. (15) becomes $$\frac{\Delta V_h(t)}{\Delta V} + \frac{\Delta V_{LW}(t)}{\Delta V} = \frac{1}{a^h}\left[1 - \frac{PA^h(t)}{PA_b^h}\right] \quad (17)$$

where $\alpha^h = (PA_b^h - PA_0)/PA_b^h$ that is always less than 1.

If the relationship between a photoacoustic signal and an isotonic dilution curve is considered on Eq. (17)

$$\frac{\Delta V_{LW}(t)}{\Delta V} = \frac{1}{a^h}\left[1 - \frac{PA^h(t)}{PA_b^h}\right] - \frac{1}{a^i}\left[1 - \frac{PA^i(t)}{PA_b^i}\right] \quad (18)$$

where $\alpha^i = (PA_b^i - PA_0)/PA_b^i$
that is known from a single isotonic curve. The superscripts h and i in Eq. (18) indicate hypertonic and isotonic solutions, respectively.

Under the assumption of that $PA_0$ is not changed, $\alpha^h$ can be found from $PA_b^h$. Also, at $t=t_e$, $\Delta V_{LW}(t_e)=0$. Therefore, $$\frac{\Delta V_h(t_e)}{\Delta V}$$

in Eq. (13) can be calculated by $$\frac{\Delta V_h(t_e)}{\Delta V} = \frac{1}{a^i}\left[1 - \frac{PA^i(t_e)}{PA_b^i}\right] - \frac{1}{a^h}\left[1 - \frac{PA^h(t_e)}{PA_b^h}\right] \quad (19)$$

The lung volume change by $t=t_e$ is the equivalent to the amount of lung water smeared into the blood from the hypertonic injection time $t_i$ to $t_e$. If the time integration is applied to both sides of Eq. (18) using $\Delta V = F \cdot dt$, $$\int_{t_i=0}^{t_e} \Delta V_{LW}(t)dt = F\left\{\frac{1}{a^h}\int_0^{t_e}\left[1 - \frac{PA^i(t)}{PA_b^i}\right]dt\right\} \quad (20)$$

where F is the blood flow rate. Therefore, from equations 19 and 20, the EVLW is Equation 13 is estimated using photoacoustic data. In this manner, the disclosed photoacoustic signal (i.e., the denoised or corrected signal from the acoustic detector 20) may be used to provide an estimate of extravascular lung water.

The disclosed embodiments are provided in the context of indicator dilution curves. However, it should be understood that the disclosed techniques may be applied to other photoacoustic monitoring systems. Further, while the disclosure may be susceptible to various modifications and alternative forms, specific embodiments have been shown by way of example in the drawings and have been described in detail herein. However, it should be understood that the embodiments provided herein are not intended to be limited to the particular forms disclosed. Rather, the various embodiments may cover all modifications, equivalents, and alternatives falling within the spirit and scope of the disclosure as defined by the following appended claims.

What is claimed is:

1. A photoacoustic monitoring system, comprising:
  a memory storing instructions for:
    receiving a first signal from an acoustic detector configured to detect a photoacoustic effect from light emitted into a patient's tissue, wherein the first signal is representative of an indicator dilution;
    receiving a second signal from a photodetector configured to detect the light, wherein the first signal and the second signal include an overlapping time period; and
    determining a physiological parameter based at least in part on the first signal and the second signal, wherein determining the physiological parameter based at least in part on the first signal and the second signal comprises using the second signal to determine a level of noise in the first signal; and
  a processor configured to execute the instructions.

2. The system of claim 1, wherein the instructions for determining the physiological parameter based at least in part on the first signal and the second signal comprise scaling the second signal to generate a scaled signal and subtracting the scaled signal from the first signal.

3. The system of claim 1, wherein the first signal and the second signal are negatively correlated.

4. The system of claim 1, wherein the physiological parameter comprises a cardiac output.

5. The system of claim 1, comprising a photoacoustic sensor comprising a light source, the acoustic detector, and the optical detector, wherein the photoacoustic sensor is configured to generate the first signal and the second signal.

6. The system of claim 5, wherein the acoustic detector and the optical detector are disposed adjacent to one another on the photoacoustic sensor.

7. The system of claim 6, wherein the light source is disposed adjacent to the acoustic detector on the photoacoustic sensor in a reflectance-type configuration.

8. The system of claim 6, wherein the light source is configured to be disposed opposite the patient's tissue relative to the acoustic detector on the photoacoustic sensor in a transmission-type configuration and wherein the first signal and the second signal are positively correlated.

9. A method, comprising:
  using a processor:
    receiving a first signal from an acoustic detector configured to detect a photoacoustic effect from light emitted into a patient's tissue;
    receiving a second signal from a photodetector configured to detect the light;
    correcting the first signal based on the second signal to generate a corrected first signal; and
    determining a physiological parameter based on the corrected first signal.

10. The method of claim 9, wherein the physiological parameter comprises a cardiac output or an extravascular lung water estimation.

11. The method of claim 9, comprising providing an indication of the physiological parameter on a display.

12. The method of claim 9, wherein correcting the first signal based on the second signal comprises scaling the second signal to generate a scaled signal and subtracting the scaled signal from the first signal.

13. The method of claim 9, comprising determining a signal quality based on a correlation between the first signal and the second signal.

14. The method of claim 13, wherein a negative correlation above a threshold is indicative of good signal quality.

15. A photoacoustic sensor, comprising:
a light emitting component configured to emit one or more wavelengths of light into a tissue of a patient;
an acoustic detector configured to detect a photoacoustic effect from the light emitted into the patient's tissue and to generate a first signal based on the detected photoacoustic effect; and
an optical detector configured to detect the light scattering through the patient's tissue and to generate a second signal based on the detected light, wherein the optical detector is disposed adjacent to the acoustic detector on the photoacoustic sensor, and wherein the first signal and the second signal are negatively correlated.

16. The photoacoustic sensor of claim 15, wherein the light emitting component comprises one or more light emitting diodes, one or more laser diodes, a pulsed laser, a continuous wave laser, or a vertical cavity surface emitting laser.

17. The photoacoustic sensor of claim 15, wherein the acoustic detector comprises an ultrasound transducer.

18. The photoacoustic sensor of claim 15, wherein a first housing of the optical detector contacts a second housing of the acoustic detector.

19. The photoacoustic sensor of claim 15, comprising an encoder disposed on the photoacoustic sensor or a cable coupled to the photoacoustic sensor, wherein the encoder is configured to store calibration information or information representative of a sensor geometry.

* * * * *